(12) United States Patent
Binachon

(10) Patent No.: US 9,987,318 B2
(45) Date of Patent: Jun. 5, 2018

(54) TNF-ALPHA INHIBITOR

(75) Inventor: Christophe Binachon, Orvault (FR)

(73) Assignee: Esprit D'Ethique, Orvault (FR)

( * ) Notice: Subject to any disclaimer, the term of this patent is extended or adjusted under 35 U.S.C. 154(b) by 578 days.

(21) Appl. No.: 14/009,665

(22) PCT Filed: Apr. 2, 2012

(86) PCT No.: PCT/EP2012/056001
§ 371 (c)(1),
(2), (4) Date: Nov. 14, 2013

(87) PCT Pub. No.: WO2012/136634
PCT Pub. Date: Oct. 11, 2012

(65) Prior Publication Data
US 2014/0065251 A1  Mar. 6, 2014

(30) Foreign Application Priority Data

Apr. 6, 2011  (FR) ...................... 11 53006

(51) Int. Cl.
*A61K 36/185* (2006.01)
(52) U.S. Cl.
CPC ...... *A61K 36/185* (2013.01); *A61K 2236/331* (2013.01)
(58) Field of Classification Search
None
See application file for complete search history.

(56) References Cited

U.S. PATENT DOCUMENTS

2010/0209572 A1* 8/2010 Guidetti ................. A23K 1/003
426/285

FOREIGN PATENT DOCUMENTS

| EP | 2 105 119 A1 * | 9/2009 |
| FR | 2 949 680 A1 | 3/2011 |

OTHER PUBLICATIONS

Amazu et al. ("Antiinflammatory activity of the methanolic extract of the seeds of Carica papaya in experimental animals", Asian Pacific Journal of Tropical Mediicine, vol. 3, No. 11, Nov. 2010 (Jan. 22, 2010)).*
Website article enititled Do you have Sinus Headaches? (http://www.ent-consult.com/sinus_head.html, copyrighted 1996,2003, 2006).*
Website article entitled Do you have Sinus Headaches? (http://www.ent-consult.com/sinus_head.html., copyrighted 1996, 2003, 2006).*
Elliott et al, "The Medicinal Plants of Gunung Leuser National Park, Indonesia," Journal of Ethnopharmacology, 1987, pp. 285-317, vol. 19.
Lu et al, "Antiinflammatory activity of the methanolic extract of the seeds of *Carica papaya* in experimental animals," Asian Pacific Journal of Tropical Medicine, 2010, pp. 884-886, vol. 3.
Nadembega et al, "Medicinal plants in Baskoure, Kourittenga Province, Burkina Faso: An ethnobotanical study," Journal of Ethnopharmacology, 2011, pp. 378-395, vol. 133.
Oladunmoye et al, "Antiinflammatory Activity of Ethanolic Leaf Extract from *Carica papaya* in Rats Orogastrically Dosed with *Salmonella typhi* and *Staphylococcus aureus*," Journal of Plant Sciences, 2007, pp. 447-452, vol. 2.
Otsuki et al, "Aqueous extract of *Carica papaya* leaves exhibits anti-tumor activity and immunomodulatory effects," Journal of Ethnopharmacology, 2010, pp. 760-767, vol. 127.
Sannella et al, "Antiplasmodial activity of papaya leaf decoction and its synergistic effects in combination with artemisinin," Planta Med, 2009, pp. 75.
Starkow et al, "Papain Therapy of Eye Diseases," Klinische Monatsblaetter Fuer Augenheilkunde, 1971, vol. 159.

* cited by examiner

*Primary Examiner* — Chris R Tate
*Assistant Examiner* — Randall Winston
(74) *Attorney, Agent, or Firm* — Muncy, Geissler, Olds & Lowe, P.C.

(57) ABSTRACT

An anti-inflammatory composition for inhibiting the secretion of cytokines, with the composition being based on a decoction of *papaya* leaves, a method of obtaining such a composition and a method of manufacturing an anti-inflammatory remedy for inhibiting cytokine secretion, having the composition the anti-inflammatory composition as its active principle. The method of obtaining the composition includes the steps of producing a decoction from *papaya* leaves, filtering the decoction in order to obtain a filtrate and atomizing the filtrate.

12 Claims, No Drawings

TNF-ALPHA INHIBITOR

The invention relates to a composition, in particular a powdered *papaya* leaf extract, used to inhibit the secretion of cytokine, and more particularly to inhibit the secretion of TNF-α.

PRIOR ART

When faced with a physical (wound), chemical (burn) or pathogenic attack, organisms respond with an inflammatory reaction. The symptoms of an inflammatory reaction are many and include redness, bleeding, fever, fatigue, loss of appetite, and pain. Those mechanisms deploy local and systemic immunological defense processes that involve many types of cell. (macrophages, lymphocytes, epithelial cells) and many biochemical pathways. Effectors of the inflammatory response include cytokines, which play a particularly important role. They are involved in intercellular exchanges and allow signals linked to the inflammation to be transmitted and allow the organism to react to the attack.

Two groups of cytokines can be distinguished: anti-inflammatory cytokines (TGF-β; IL6), which act to reduce inflammation, and pro-inflammatory cytokines (TNF-α, IL6, IL1β), which are involved in amplification and systemization of the organism's response.

In order to combat symptoms linked to inflammation, in particular pain and fever, anti-inflammatory substances are mainly used, based either on glucocorticoids, or on non-steroidals such as aspirin.

In particular, such anti-inflammatory substances act by inhibiting the synthesis of prostaglandins, which are important mediators in inflammatory phenomena. Regardless of whether or not the anti-inflammatories are steroidal, they weaken the stomach wall, and even in small doses they are responsible for stomachaches, a side effect that is sometimes poorly tolerated.

Thus, alternatives to such anti-inflammatory substances acting on other metabolic pathways are being sought. Monoclonal antibodies or recombinant proteins blocking pro-inflammatory cytokines have been under development for a number of years. However, they are still very difficult and very expensive to produce and administer. Such novel treatments are thus reserved for chronic inflammatory diseases.

OBJECT OF THE INVENTION

An object of the invention is to propose a composition that is anti-inflammatory by inhibiting the secretion of cytokines, that is easy to produce and to administer, and that can be used to act on the anti-inflammatory reaction, and thus on the symptoms of inflammation.

SUMMARY OF THE INVENTION

In order to achieve this object the invention provides a composition based on a decoction of *papaya* leaves used as an anti-inflammatory agent.

The composition is preferably used as an agent for inhibiting the secretion of cytokines, in particular of tumor necrosis factor alpha (TNF-α).

The composition of the invention is effective for inflammatory reactions affecting the mucous membranes, the conjunctiva, or the skin. The composition of the invention may be used against inflammatory reactions in any organism, in particular those of the human organism, but it may also be used to reduce inflammatory reactions in other organisms such as mammals (for example dogs, cats, horses, etc.).

Application of a composition of the invention is particularly effective as it acts as an anti-inflammatory agent for the ENT region, encompassing the ears, nose, mouth, and throat. It is particularly effective in reducing, limiting, or curbing inflammatory reactions of the mouth such as gingivitis or periodontitis, or of the nose such as sinusitis or rhinitis.

Advantageously, the composition is packaged in a manner such that it can be nebulized or instilled onto the inflamed zone.

The composition of the invention may be in the form of a powder, a tablet, or a suspension in an aqueous solution.

The present invention also provides a method of obtaining said composition, consisting in producing a decoction from *papaya* leaves, of filtering the decoction obtained thereby, and then of atomizing the filtrate. More precisely, the method of the invention comprises the steps of drying the *papaya* leaves, and grinding them. The ground material is then immersed in a volume of water corresponding by weight to 30 times the weight of the ground material. Next, the mixture of water and ground dried *papaya* leaf material is decocted for at least one hour at a temperature of at least 90° C., preferably 95° C. It is then possible to filter the decoction to 100 micrometers (μm).

This manufacturing method is particularly convenient for obtaining an effective anti-inflammatory composition.

In a preferred implementation of the method of the invention, the decoction is then atomized in a nozzle atomizer with an inlet temperature of 300° C. and an outlet temperature of 105° C. This step may be preceded by a step of concentrating or vacuum evaporating the filtrate.

The present invention also provides a method of manufacturing an anti-inflammatory remedy, in particular by inhibiting the secretion of cytokines, having the composition of the invention as its active principle.

DETAILED DESCRIPTION OF THE INVENTION

Papaya (*Carioca papaya* L.) is a plant that is known for its many nutritional and therapeutic benefit, principally due to it being rich in vitamins A and E and in proteolytic enzymes.

It is thus well known that the fruit, along with the latex contained in the sap of the plant, have high concentrations of papain and chymopapain, which are proteolytic enzymes. For this reason, fruits and fresh leaves are routinely used to facilitate digestion. In traditional medicines, fresh leaves are also sometimes used as local anti-inflammatories. In fact, papain and chymopapain have a fibrinolytic activity, which means that the edema formed during certain inflammatory reactions can be reduced. Thus, all compositions based on parts of the *papaya* are intended to conserve and concentrate these two proteolytic enzymes.

The composition of the invention is a decoction of *papaya* leaves used as an anti-inflammatory agent. The effect of carrying out the decoction at 95° C. is to destroy the proteolytic enzymes, thereby rendering them inactive. Preferably, said composition is a dry extract obtained after decocting *papaya* leaves and is used as an anti-inflammatory agent.

The inventors have shown that application to inflamed regions of the composition of the invention based on a dry extract obtained by decocting dried *papaya* leaves results in curbing propagation of the inflammation and in limiting symptoms, and then after several daily applications, in reducing or even eliminating the inflammation.

The term "inflammation" encompasses all of the inflammatory reactions of the organism in response to an external attack: whether it is mechanical, e.g. a wound or a blow; chemical, e.g. a burn; or biological, e.g. an infection by pathogenic agents, such as an infection caused by bacteria, viruses, or fungi.

The inventors have demonstrated that the composition of the invention inhibits secretions of pro-inflammatory cytokines, in preferred manner of TNF-α secretions, and can thus be used to attenuate or even completely resorb the inflammation, and can do so in the absence of proteolytic enzymes such as papain or chymopapain. They have also demonstrated that applying this composition increases the pH of the inflamed zone and thus limits bacterial proliferation and hence inflammation, in particular in the mouth.

The term "curb" means that propagation of the inflammation is slowed down.

The term "limiting" inflammatory reactions means that propagation of the inflammation is "prevented" in terms both of time and of extent.

The term "attenuating" or "reducing" inflammation means that manifestations or symptoms of inflammation such as hypersensitivity of the inflamed zone, pain, redness, and bleeding due to hypervascularization are substantially reduced. The attenuation or reduction may go as far as complete disappearance or resorption of symptoms of the inflammation.

Particularly effectively, the composition of the invention may be used as an anti-inflammatory agent in inflammations of the ENT region, i.e. inflammations affecting the ears, mouth, nose, and throat. In particular, the present composition can be used to reduce, limit, or curb inflammatory reactions of the mouth such as, by way of non-limiting example, gingivitis orperiodontitis, of the nose such as, by way of non-limiting example, rhinitis or sinusitis, or of the ears such as, by way of non-limiting example, otitis.

The composition may also be used in inflammations of other organs, non-limiting examples of which that may be mentioned being the mucous membranes, the conjunctiva, the eye, the skin, the joints, etc.

Preferably, the composition based on a dry extract of *papaya* decoction of the invention is in the powder form. The powder may be used as such in gelules, or it may be compressed to produce tablets. The skilled person is able to add other compounds such as, by way of non-limiting example, vitamins, antibiotics, flavors, preservatives, or any other active compound. Preferably, the powder can be compressed to produce dispersible tablets (water-dispersible or orally disintegrating), making them easier to take. The skilled person is able to select the most suitable disintegration agent. By way of example, sodium starch glycolate, wheat or corn starch, or pre-gelatinized starch may be selected.

Highly preferably, the powder is taken up into suspension in an aqueous solution. This solution may then be used, for example as a mouthwash or gargle. The Skilled person knows how to adapt the concentration of the solution to the desired use, in particular if it is an initial therapy or background therapy.

Depending on the inflamed zone concerned, the composition may be packaged into the form of an ointment or a gel, for direct application to the inflamed zone. It may also be packaged in the form of a spray, nebulizer, or aerosol for better application into the nose, mouth, or throat.

The composition may also be dissolved in order to be instilled into inflamed organs such as the ear or the eye.

The present invention also provides a method of obtaining a composition based on a decoction of *papaya* leaves used as an anti-inflammatory agent. Said method comprises the following steps:
producing a decoction from *papaya* leaves;
filtering the decoction; and
atomizing the filtrate.

Producing the decoction comprises the steps of drying the *papaya* leaves then grinding them. The ground material obtained is then weighed and immersed in a volume of water equivalent in weight to 30 times the weight of the ground material. The mixture of water and ground dried *papaya* leaves is then heated to a temperature of at least 90° C., preferably 95° C., for approximately one hour. This step corresponds to the decoction step. Filtration to 100 μm is then carried out. The filtration step may be preceded by a centrifuging step. The supernatant is filtered. Filtration may be carried out under vacuum in order to accelerate the process thereby. Preferably, the method of the invention comprises a step of concentrating the filtrate. The concentration step may be carried out under vacuum until the concentration is 20% to 30% higher relative to the filtrate.

After this step it is possible to add an inert support to allow adsorption of the composition of the invention. In a non-limiting manner, this support may be constituted by pumice stone, clay, gum Arabic, or polysaccharides, depending on the envisaged applications and on the corresponding mode of administration. The support is preferably constituted by grains coated with the composition of the invention.

The filtrate, the concentrated filtrate, or the supplemented filtrate is then atomized in a nozzle evaporator with an inlet temperature in the range 200° C. to 300° C. and a maximum outlet temperature of 105° C. In equivalent manner, this atomization step may be carried out in a high speed rotary evaporator with identical inlet and outlet temperatures.

If the composition is not intended to be used in the days following its manufacture, it is necessary to sterilize it, for example by heating, in particular by pasteurizing.

Finally, the present invention provides a method of manufacturing an anti-inflammatory remedy, in particular by inhibiting the secretion of cytokines, having the composition of the invention as the active principle.

EXAMPLES

1—Obtaining a Composition Based on a Decoction of Papaya Leaves, Used as an Anti-Inflammatory Agent 5 kilograms (kg) of dried and ground *papaya* leaves were immersed in 150 liters (L) of water. This solution was then heated for 1 hour at 95° C. then filtered to 100 μm.

The filtrate obtained thereby was concentrated in order to obtain a dry matter content in the range 25% to 30%, then atomized in a nozzle evaporator with an inlet temperature of 300° C. and an outlet temperature of 105° C.

A little more than one kilogram of the composition of the invention was obtained.

2—Measurement of Anti-Inflammatory Activity by Inhibition of TNF-α Secretion

The anti-inflammatory activity of the composition (hereinafter termed G1B) thus obtained was measured on human THP-1 cells obtained from an acute monocytary leukemia. The THP-1 cells were seeded to a high density onto culture microplates in the presence of a concentration range for the composition of the invention (2-1-0.5-0.25-0.125-0.0625-

0.0313 milligrams per milliliter (mg/mL)) and placed in an incubator at 37° C., under 5% $CO_2$.

After overnight incubation, the THP-1 cells were stimulated by adding LPS, to 5 micrograms per milliliter (μg/mL) final.

After 4 hours of incubation, the supernatant was recovered and the quantity of TNF-α therein was assayed using an ELISA test. The results are expressed as a % inhibition relative to the untreated control and they are summarized in Table 1.

TABLE 1

Percentage inhibition of TNF-α secretion by THP-1 cells stimulated with LPS as a function of the concentration of G1B

| Concentration of G1B (mg/mL) | Percentage of TNF-α secreted relative to control |
| --- | --- |
| Control (no G1B) | 100 |
| 0.0313 | 90 |
| 0.0625 | 74 |
| 0.125 | 49 |
| 0.25 | 22 |
| 0.5 | 6 |
| 1 | 3 |
| 2 | 4 |

Strong inhibition of TNF-α secretion by THP-1 cells stimulated with LPS was observed for the composition of the invention. The inhibition was dose-dependent and could be detected beyond a dose of 0.03 mg/mL. It reached 50% at a dose of 0.125 mg/mL. When the concentration of the composition of the invention was 0.5 mg/mL, inhibition of the secretion of TNF-α was almost total.

A MTT cell viability test was carried out on the corresponding cells in order to validate the results. The analyses confirmed the viability of the cells for all of the experimental conditions.

3—Measurement of Anti-Inflammatory Activity of the Composition of the Invention on Gingivitis A mouthwash solution composed of a pinch of powder obtained in Example 1 was made up in a glass of water.

The pH measured in the mouth before the treatment was less than 5.

The patient, who had gingivitis, had daily mouthwashes with the aqueous solution obtained.

After this treatment, the measured pH of the mouth was more than 5.

A significant reduction in the bleeding index was observed in the gums. Bleeding disappeared after two-three days.

4—Measurement of Anti-Inflammatory Activity of the Composition of the Invention on Rhinitis The composition of the invention was inhaled either directly or dispersed into the nostrils using a spray device in an amount of two sprays per day.

After a few minutes, the inflammation had reduced substantially.

Clearly, the invention is not limited to the above description, but in contrast encompasses any variation within the ambit defined by the claims.

The invention claimed is:

1. A method for inhibiting the secretion of TNF-α during an inflammatory reaction in a subject in need thereof, comprising:
    preparing a composition based on a decoction of dried *papaya* leaves, including the steps of:
        grinding the dried *papaya* leaves;
        immersing in a volume of water the ground dried *papaya* leaves;
        heating the mixture of water and ground dried *papaya* leaves to a temperature of at least 95° C., for approximately one hour;
        filtering the decoction in order to obtain a filtrate; and
        atomizing the filtrate in order to obtain the composition in the form of powder; and
    administering an effective amount of the said composition to a patient suffering from the inflammatory reaction by inhibiting the TNF-α secretion.

2. The method according to claim 1, wherein the inflammatory reaction is localized in the ENT region.

3. The method according to claim 2, wherein the inflammatory reaction is caused by an infection of the mouth such as gingivitis or periodontitis.

4. The method according to claim 3, wherein the inflammatory reaction is caused by an infection of the nose such as rhinitis or sinusitis.

5. The method according to claim 1, wherein the inflammatory reaction is localized in the eye region.

6. The method according to claim 1, wherein the ground and dried *papaya* leaves are immersed in a volume of water corresponding by weight to 30 times the weight of said ground dried *papaya* leaves.

7. The method according to claim 1, wherein the filtration of the decoction is carried out to 100 mm.

8. The method according to claim 1, wherein prior to the step of atomizing the filtrate, a concentration or vacuum evaporation of the filtrate is performed for a predetermined period and the atomization is carried out in an atomizer with a maximum outlet temperature of approximately 105° C.

9. The method according to claim 1, wherein during the step of administering to the subject an effective amount of the said composition, said composition is in the form of powder suspended in an aqueous solution.

10. The method according to claim 1, wherein during the step of administering to the subject an effective amount of the said composition, said composition is wherein during the step of administering to the subject an effective amount of the said composition, said composition is packaged into the form of tablets.

11. The method according to claim 1, wherein during the step of administering to the subject an effective amount of the said composition, said composition is administered by nebulization onto an inflamed zone of the subject.

12. The method according to claim 1, wherein during the step of administering to the subject an effective amount of the said composition, said composition is administered by instillation onto an inflamed zone of the subject.

* * * * *